(12) United States Patent
Pritchett

(10) Patent No.: US 8,859,016 B2
(45) Date of Patent: *Oct. 14, 2014

(54) SONICALLY FORMED TRICHOMIC EXTRACT MATERIAL

(71) Applicant: Graham Bryan Pritchett, Dillon, CO (US)

(72) Inventor: Graham Bryan Pritchett, Dillon, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/248,744

(22) Filed: Apr. 9, 2014

(65) Prior Publication Data

US 2014/0212518 A1    Jul. 31, 2014

Related U.S. Application Data

(62) Division of application No. 13/679,953, filed on Nov. 16, 2012, now Pat. No. 8,728,544.

(51) Int. Cl.
*A01N 65/00* (2009.01)
*A61K 36/185* (2006.01)
*A61J 3/00* (2006.01)

(52) U.S. Cl.
CPC . *A61K 36/185* (2013.01); *A61J 3/00* (2013.01)
USPC .......................................................... 424/725

(58) Field of Classification Search
None
See application file for complete search history.

(56) References Cited

U.S. PATENT DOCUMENTS

| | | |
|---|---|---|
| 3,113,225 A | 12/1963 | Kleesattel |
| 3,602,257 A | 8/1971 | Berleyoung |
| 3,939,033 A | 2/1976 | Grrgach |
| 4,097,327 A | 6/1978 | Calemard |
| 4,131,505 A | 12/1978 | Davis, Jr. |
| 4,582,239 A | 4/1986 | Scotto |
| 4,601,927 A | 7/1986 | Durfee |

OTHER PUBLICATIONS

Pritchett, Graham, Ultrasonic Vibration-Assisted Pelleting of Sorghum Stalks: Effects of Pressure and Ultrasonic Power, Proceedings of the ASME 2010 International Manufacturing Science and Engineering Conference MSEC2010, Oct. 12-15, 2010, 7 pgs, MSEC2010-34173, Erie, Pennsylvania, USA.

Q. Feng., An Experimental Study on Temperature in Ultrasonic Vibration-Assisted Pelleting of Cellulosic Biomass, Proceedings of the 2010 ASME International Manufacturing Science and Engineering Conference MSEC2010, Oct. 12-15, 2010, 6 pgs, MSEC2010-34148, Erie, Pennsylvania, USA.

Q. Feng., An experimental study on charring of cellulosic biomass in ultrasonic vibration-assisted pelieting, Int. J. Manufacturing Research, vol. 6, No. 1. 2011, pp. 77-86.

Pritchett, Graham, Ultrasonic-Virastion Assisted Pelleting for Cellulosic Ethanol Manufacturing: An Experimental Investigation Of Power Consumption, Proceedings of the ASME 2011 International Mechanical Engineering Congress and Exposition IMECE2011, November 11-17, 2011, 9 pgs, IMECE2011-64307, Denver, Colorado, USA IMECE2011-64307.

*Primary Examiner* — Michael Meller
(74) *Attorney, Agent, or Firm* — Will Hunziker

(57) ABSTRACT

A process, product, and product by process related to sonic welding, for quickly, compressing, shaping, and decarboxylating cannabinoids; preferably from Cannabis; for oral ingestion without using any liquids or solvents; such process breaks down the Cannabis plant's cellulosic structure; increasing oil extraction; while compaction decreases transportation and storage costs, making the end product desirable as an additional ingredient in other edibles.

10 Claims, 7 Drawing Sheets

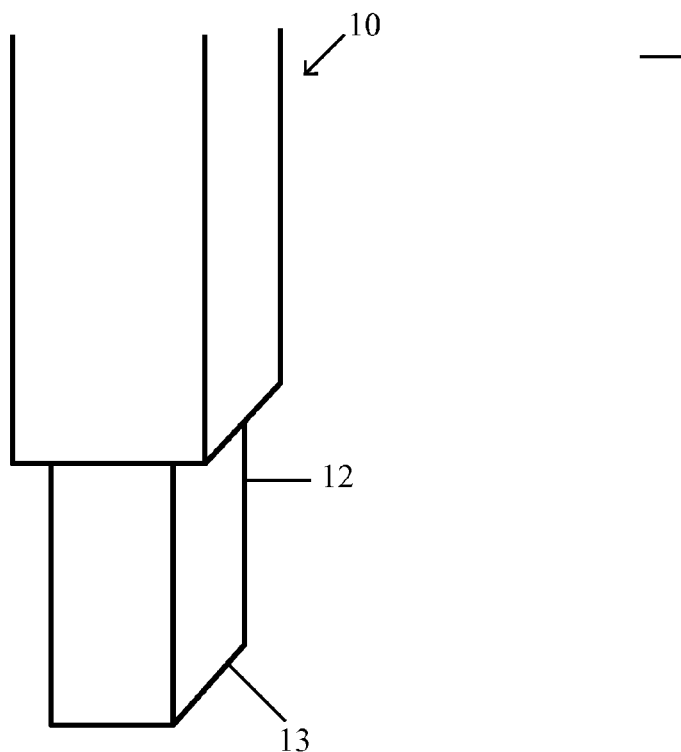
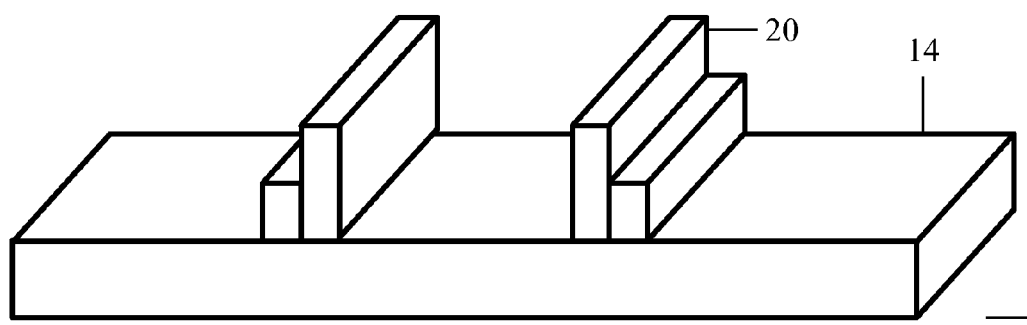
Fig. 1

SONICALLY FORMED TRICHOMIC EXTRACT MATERIAL

CROSS-REFERENCE TO RELATED APPLICATION

The document is a divisional patent application claiming priority to, and the benefit of, U.S. patent application Ser. No. 13/679,953, filed Nov. 16, 2012, also entitled "Sonically Formed Trichromic Extract Material," which is herein incorporated by reference in its entirety for all purposes.

BACKGROUND OF THE INVENTION

1. Field of the Invention

The present invention is in the technical field of ultrasonic biomass pelleting. More particularly, the present invention pertains to sonically welded or formed Cannabis trichome containing materials and the oral activation, or decarboxylation, of tetrahydrocannabinol (THC), cannabidiol (CBD), cannabinoids, and analogous compounds based on Cannabis materials.

2. Description of Related Art

Cannabinoids derived from Cannabis have long been used for medicinal and recreational purposes. Tetrahydrocannabinol (THC) is generally considered to be the primary active substance in Cannabis; however, THC must first be decarboxylated from its precursor tetrahydrocannabinolic acid (THCA) to become psychoactive. The carboxyl group of THCA is released from the molecule as carbon dioxide and water vapor at around 106° C. (220° F.), while the resultant THC and other cannabinoids have a boiling point of between 180 and 200° C. (355 and 392° F.).

Decarboxylation is often accomplished by drying the cannabinoid rich trichome of the Cannabis plant, heating it to combustion, then inhaling the resultant gases. This method of consumption can be harmful due to the inhalation of noxious particulate matter and gases; for this reason many consumers prefer to ingest their cannabinoids orally. Additionally, many consumers report a slower onset and longer active duration of the psychoactive cannabinoids in Cannabis when ingested orally.

Along with other psychoactive cannabinoids, THC is a hydrophobic oil, meaning it's insoluble in water but soluble in lipids (oil/fat) and alcohol. Traditional activation of the psychoactive compounds of Cannabis for oral ingestion typically involves making oils, butters, or liqueurs by first dissolving the tetrahydrocannabinol (THC), cannabidiol (CBD), cannabinoids, and analogous compounds into a liquid—often through cooking the Cannabis in the solvent. A description of these solvent based methods follows.

"Cannaoils" or "marijuana oils" are cooking oil based products that have been infused with cannabinoids. This is accomplished by performing a cannabis extraction into the oils through various methods. Cannabis cooking oils are available for various cooking applications. The extraction process can be as easy as using a frying pan or pot, double-boiler, or a slow cooker. Cannaoils can be used in any recipe that calls for oil and that doesn't go above the temperature at which THC is vaporized.

"Cannabutter" or "marijuana butter" is a butter-based solution which has been infused with cannabinoids. This is achieved by heating the raw cannabis material along with butter and allowing the cannabinoids to be extracted by the lipids in the butter. The equipment necessary for the manufacture of cannabutter can be as simple as a sauce pan and spatula or as complicated as a double-boiler, or slow cooker, cheesecloth or tea strainer and funnel. Cooking time varies from 10-15 minutes to 24 hours, depending on the amount of cannabis used and the temperature it is cooked at.

Because cannabis resins are soluble in alcohol, cannabinoids are capable of being infused into liquids in proportion to the alcohol content of such liquids; such infusion is typically not heated as alcohol has a very low boiling temperature. Absorption of cannabinoids by alcohol can take a very long time. When ready, the consumer can drink the alcohol, or add it as an ingredient in their cooking The problem with each of the common methods of producing orally active cannabinoids is that they are time consuming, laborious, and the end product is a liquid which can be harder to store, move, or process into new products.

SUMMARY

Embodiments of the present invention describe an apparatus, a process, and a product by process relating sonic welding of Cannabis trichome containing materials and the decarboxylation, or oral activation, of psychoactive cannabinoids (i.e. tetrahydrocannabinol (THC), cannabidiol (CBD), and analogous compounds) or extracts of the Cannabis plant for oral ingestion using a high frequency sonic welding tool apparatus. Additionally, the high frequency sonic welding tool apparatus breaks down the Cannabis plant's cellulosic structure, increases oil extraction, and decreases transportation costs.

Embodiments of the disclosed methods include the use of an ultrasonic vibration assisted welding apparatus to achieve the desired temperature and compression. The sonic welding tool can be selected by anyone versed in the art of ultrasonic biomass pelleting with an emphasis on temperature regulation. The sonic welding tool can be any such ultrasonic welding device fitted with external or internal means of applying force and vibration energy to the cannabinoid containing material.

Embodiments of the disclosed products, processes, and products by processes may use any cannabinoid containing material, such as, but not limited to: granular trichome extract material, moisture adjusted Cannabis flowers, moisture adjusted Cannabis material, or a combination of such materials. The material can be placed in a channel or hole of a rigid mold apparatus that can be fixed to a sonic welding area base plate of a sonic tool with any commonly known means for securing said rigid mold apparatus to said sonic welding area base plate. The sonic tool can be fitted with hydraulic, pneumatic, or other means commonly known to the art in order to apply pressure to the cannabinoid containing material in the channel or hole of the rigid mold apparatus by applying pressure with the bottom surface of such sonic tool. The sonic welding tool is then activated such that vibrations can move bidirectional and perpendicular to a sonic welding area base plate.

Pressure and frictional forces from the sonic welding tool can easily generate temperatures exceeding 110 degrees Celsius in the material placed in the channel or hole of the rigid mold apparatus. The Cannabis materials containing cannabinoid compounds, such as THCA, then become decarboxylated above 110 degrees Celsius making the product of the process psychoactive.

After a predetermined time or sonic welding apparatus energy consumption; based upon the material temperature gain; the sonic welding tool can be retracted and the sonically formed psychoactive cannabis product can be removed from the rigid mold apparatus. The time or energy applied to the material should be regulated in accordance with the temperature of the material during the process allowing for decarboxylation of the cannabinoid compounds without exceeding their boiling point. Optimal frequencies, pressures, and durations for regulating the temperature of the material during the process are dependent on local conditions and equipment should be adjustable for variable conditions or set up for location. Because results depend upon the local environment, pressure, temperature, and altitude careful attention should be given to optimizing each of the variable to produce an optimal product. Typical safe operating material temperature for decarboxylating cannabinoids is about 110 to 190 degrees Celsius.

Product of embodiments of the disclosed methods may be cannabinoid containing material that is: uniform, solid, compressed, multi-dimensional, decarboxylated and psychoactive material appropriate for oral consumption that has a higher density than the original material. While the basic benefits of compressing the materials (increased density, efficient storage, and lower transportation costs) apply to any material, the ultrasonic processing method performs the added step of decarboxylating the cannabinoids in the material for oral consumption. An added benefit is that the process simultaneously sterilizes the product.

OBJECTS AND ADVANTAGES

The present disclosure can provide a number of advantages depending on the particular aspect, embodiment, and/or configuration. None of the particular objects or advantages that follow must be entirely satisfied as they are non-exclusive alternatives and at least one of the following objects is met; accordingly, several objects and advantages of the present invention are:

(a) to provide a means for increasing the psychoactive properties of cannabinoid containing material;

(b) to provide a means for decarboxylating cannabinoid containing material;

(c) to provide a means for decarboxylating cannabinoid containing material that is dry and does not involve using alcohol or oils as solvents;

(d) to provide a means for sterilizing cannabinoid containing material;

(e) to provide a means for compressing cannabinoid containing material;

(f) to provide a means for breaking down the cellulosic structure of cannabinoid containing material;

(g) to provide a means for increasing oil extraction from cannabinoid containing material;

(h) to provide a means for decreasing the costs of transporting cannabinoid containing material;

(i) to provide a means for decreasing the costs of storing cannabinoid containing material;

(j) to provide a means for accomplish all the list items above quickly;

(k) to provide a means for quickly creating a uniform compressed solid made of decarboxylated cannabinoid containing material that can be used as an ingredient in other products.

These and other objectives and advantages of the instant invention will become apparent from the following description taken in conjunction with the accompanying drawings wherein are set forth, by way of illustration and example, certain embodiments of the instant invention. The drawings are intended to constitute a part of this specification and include exemplary embodiments of the present invention and illustrate various objects and features thereof.

BRIEF DESCRIPTION OF THE DRAWINGS

1. Figures

FIG. 1 (Sheet 1) illustrates a perspective view showing a sonic welding apparatus and sonic welding area base plate, according to embodiments of the present invention.

DETAILED DESCRIPTION OF A PREFERRED EMBODIMENT

1. Preamble

Figure 2:
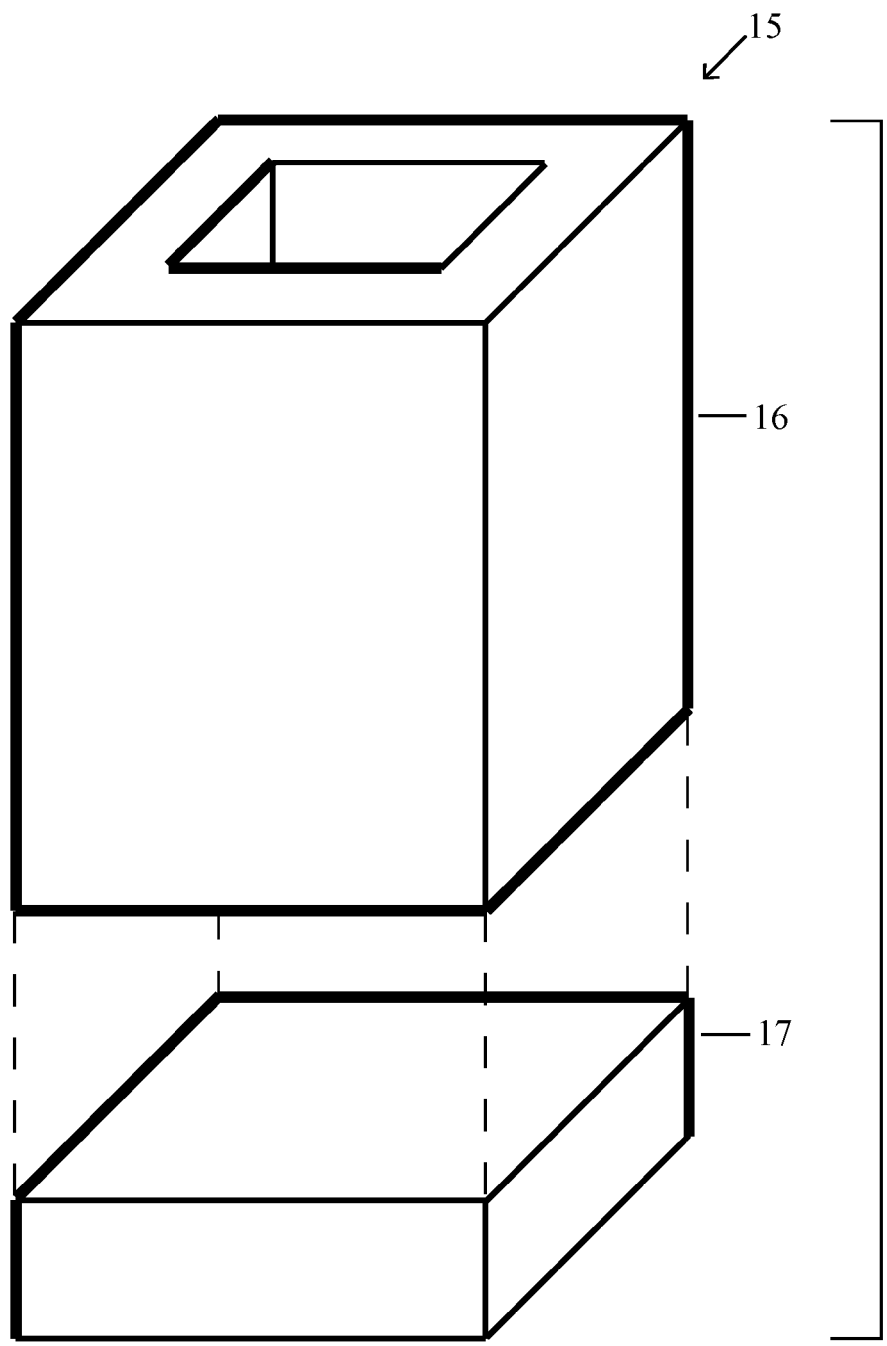
FIG. 2 (Sheet 2) illustrates an exploded perspective view showing a rigid mold apparatus, according to embodiments of the present invention.

For the purposes of promoting an understanding of the principles of the present invention, reference will now be made to the embodiments illustrated in the drawings and specific language will be used to describe the same. However, the illustrated embodiments are merely exemplary and many additional embodiments of this invention are possible. It is understood that no limitation of the scope of the invention is thereby intended. Any alterations and further modifications in the illustrated devices, and such further application of the principles of the invention as illustrated herein are contemplated as would normally occur to one skilled in the art to which the invention relates.

Unless otherwise indicated, the drawings are intended to be read (e.g., arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

The phrases "at least one," "one or more," and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. The terms "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

This invention discloses an apparatus, a process, and a product by process relating sonic welding. It should be understood that the process need not proceed from one step to the next in the specific order described below and that the process need not involve all the steps described below. For example, the cannabinoid containing material can be weighed after placing it in the rigid mold apparatus, or not weighed at all. Likewise, adjustments to the sonic welder can be made before or after attachment of the rigid mold apparatus to the sonic welding area base plate.

The words "sonic" and "ultrasonic" and derivatives thereof, are intended to be used interchangeably to describe vibrations of a character suitable for performing the welding operation of this invention. For example, the frequencies may have a range of from 15,000 to 40,000 vibrations per second, but the end results of the process are determined by the combination of all variables: duration, pressure, amplitude, frequency, and temperature.

2. Description

The preferred embodiment of the present invention relates to an apparatus, a process, and a product by process relating sonic welding of Cannabis trichome containing materials and the decarboxylation, or oral activation, of psychoactive cannabinoids; however, the invention can be practiced with any cannabinoid containing material. Additionally, the cannabinoid containing material can be simultaneously sonically formed into a uniform pellet, wafer, tab, mass, or uniform compact solid of almost any consumable dimension by applying the proper pressure in combination with sonic vibration along a pressing axis perpendicular to a sonic welding area base plate. Attentive calibration, standardized operating procedures, and reclamation techniques help minimize loss of material.

Figure 5:
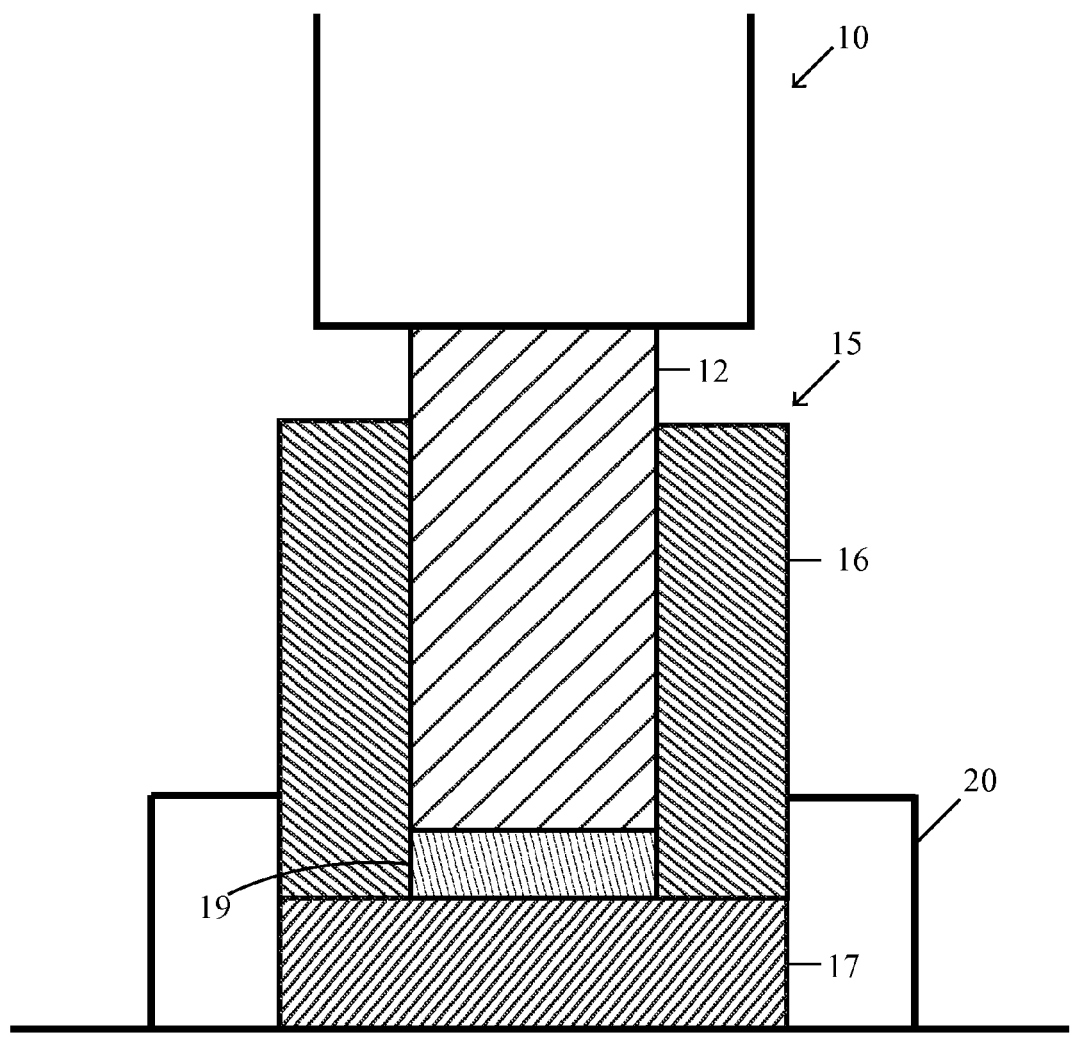
FIG. 5 (Sheet 5) illustrates a sonic welding tool apparatus with cannabinoid containing material under compression, according to embodiments of the present invention.
Figure 6:
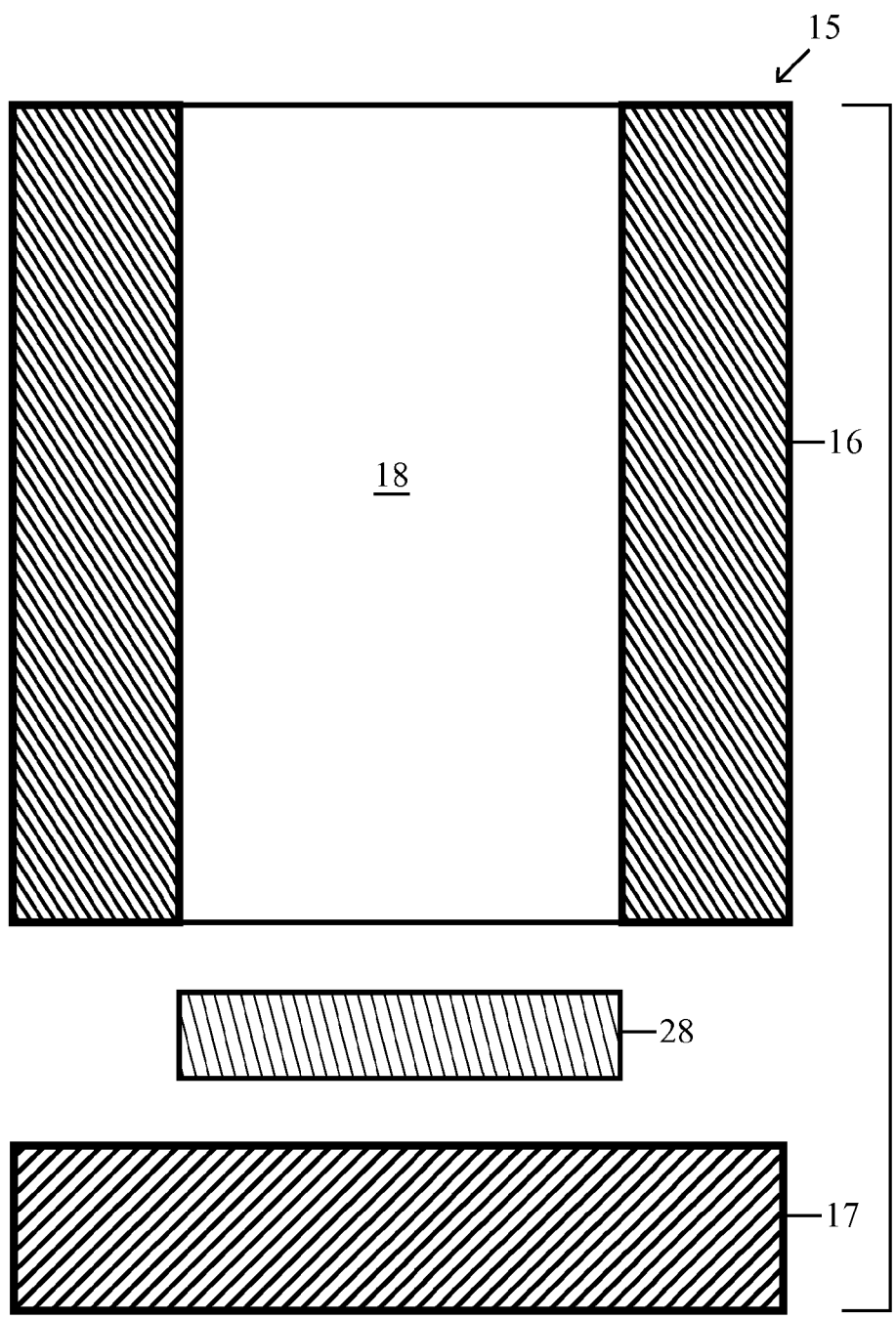
FIG. 6 (Sheet 6) illustrates an exploded cross-section view of compressed uniform solid of cannabinoid containing material and a rigid mold apparatus, according to embodiments of the present invention.
Figure 7:
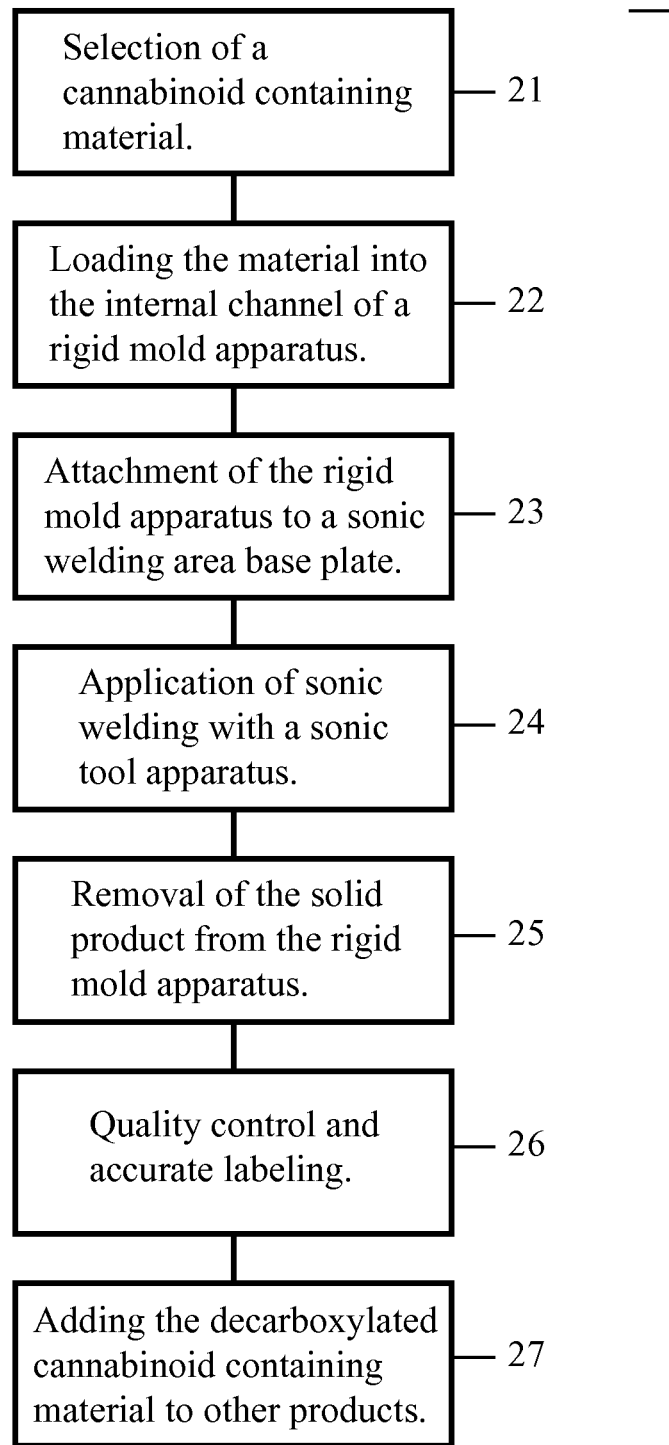
FIG. 7 (Sheet 7) illustrates a flow chart comprising the steps for processing cannabinoid containing materials using a sonic welding tool, according to embodiments of the present invention.

An embodiment comprising the steps of the process as a whole is illustrated in FIG. 7, while the machinery and materials used in the process are described in FIGS. 1 through 6.

In an embodiment of the present invention, the first step (21) in the process of manufacturing the product is selecting a cannabinoid containing material. This step comprises selecting a cannabinoid containing material (9), shown in FIG. 4; preferably the dried trichome material of a Cannabis plant. Such cannabinoid containing material (9) may be readily selected by anyone skilled in the art of extracting and refining Cannabis. In addition to the cannabinoid containing material, any other desirable material may be added to create a material that still comprises cannabinoid containing material.

Additionally, the cannabinoid containing material (9) should be massed according to the desired specifications. Mass should be changed while adjusting for tool head size and desired pellet thickness, some commonly used commercial measurements are 0.5 grams, 1 gram, 3.5 grams, 7 grams, 14 grams, 28 grams, 100 grams, ¼ pound, ½ pound, 1 pound, ½ Kilogram, 1 Kilogram, etc. This can be accomplished by hand, using a scale to determine weight, or with an automated filling procedure that includes a regulated means of distributing the cannabinoid containing material (9) into the rigid mold apparatus (5). The material should be weighed before being loaded into a rigid mold apparatus as some adjustment will be necessary in accounting for loss of material during the loading, sonic compression, and unloading stages of the material.

Figure 3:
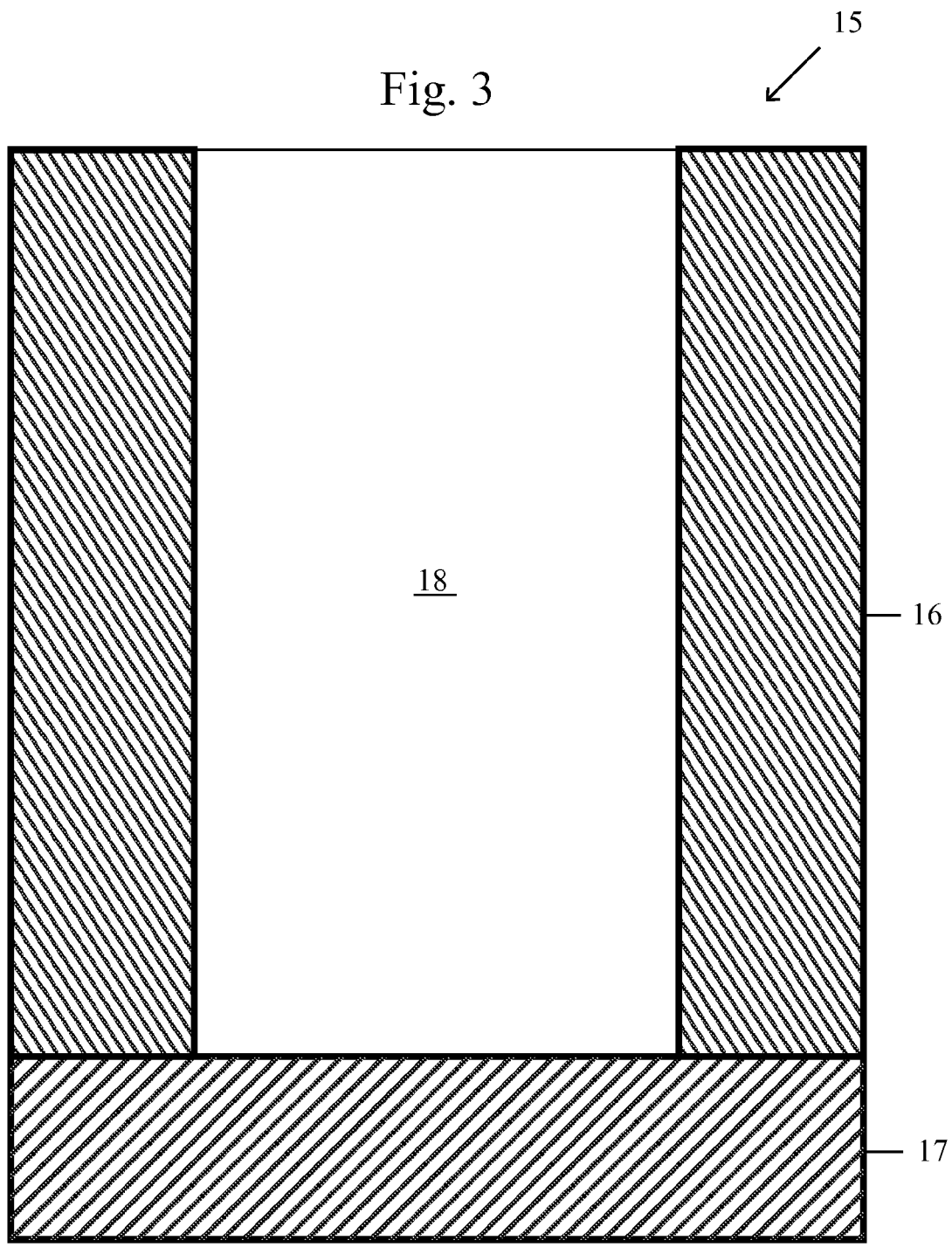
FIG. 3 (Sheet 3) illustrates a cross-section of a rigid mold apparatus, according to embodiments of the present invention.
Figure 4:
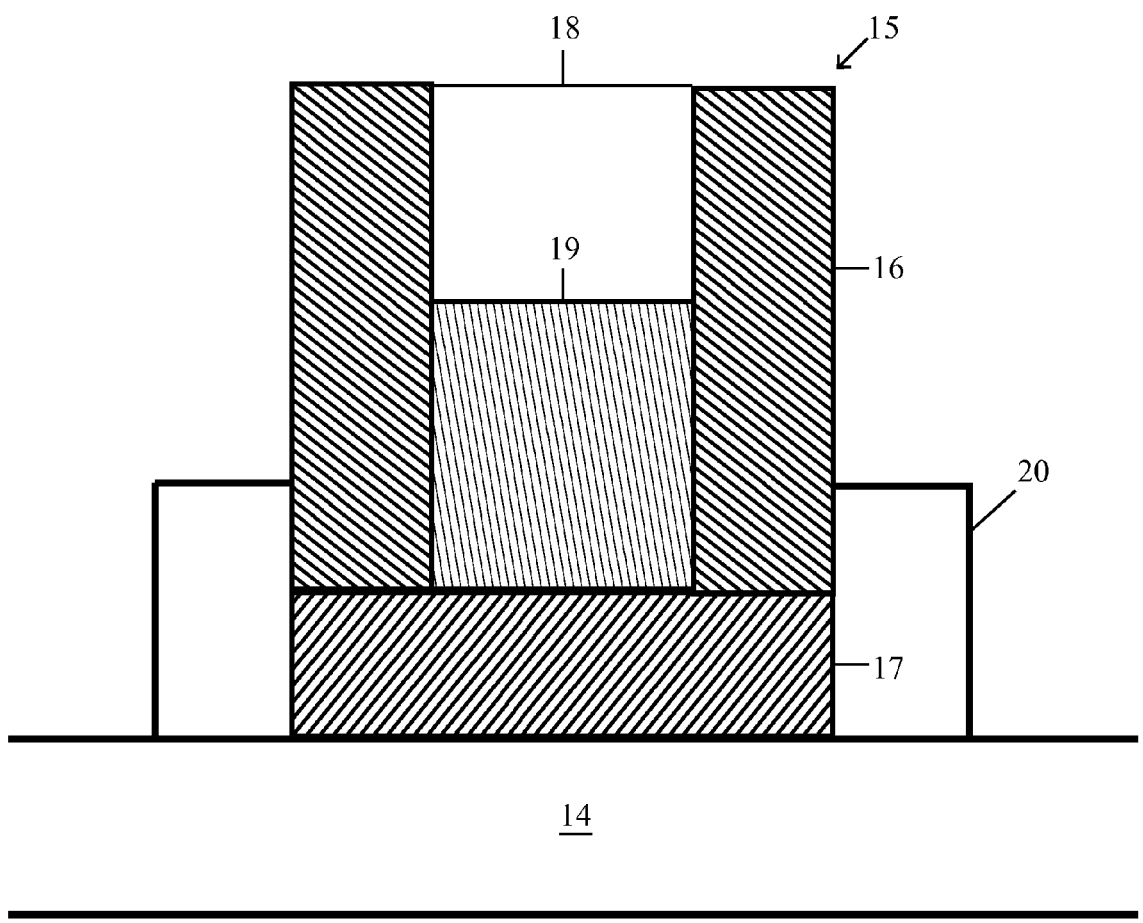
FIG. 4 (Sheet 4) illustrates a cross-section of cannabinoid containing material in a rigid mold apparatus, resting on a sonic welding area base plate, according to embodiments of the present invention.

In an embodiment of the present invention, the second step (22) in the process of manufacturing the product is loading the cannabinoid containing material (9) into an internal channel (18) of a rigid mold apparatus (15), a cross-section of one such embodiment is illustrated in FIG. 3. This rigid mold apparatus (15) can be made of any material suitable to its purpose and designed by anyone familiar with the insertion tolerances for side-to-side vibration (as opposed to bidirectional vertical vibrations) in ultrasonic welding tools. This step provides a structure for containment of the cannabinoid containing material (9) while applying sonic vibrations with the sonic welding apparatus and compression forces with hydraulic, pneumatic, or other means known to produce compression in the art. The rigid mold apparatus can be constructed for ease of removal of the cannabinoid containing material as illustrated in FIG. 2, where an upper portion (16) of the rigid mold apparatus (15) can be detached from a lower portion (17) allowing the cannabinoid containing material to be removed easier, or by any means known in the art for separating a rigid mold apparatus for ease of cleaning or removal of material therein.

The rigid mold apparatus can be of any shape or configuration that will allow the sonic horn (12), illustrated in FIGS. 1 and 5 to enter the rigid mold apparatus channel (18) and compress the material (9) into a confined space. The shape and design of this rigid mold apparatus (15) is dependent upon the desired shape and size of the end product. More complicated molds that include patterns or stamps can be used; but this may, depending on complexity, require the addition of a foil lining or other means of assisting in the removal the finished pellet. During an automated process the rigid mold apparatus (15) can be used in multiplicity to form a continuous production cycle, where the sonic horn (12) moves into the channel (18) of a new rigid mold apparatus (15) as the production line moves forward. A worker, a semi, or a fully automated means can be used to load and unload material from the rigid mold apparatus (15).

In an embodiment of the present invention, the third step (23) in the process of manufacturing the product is attachment of the rigid mold apparatus (15) to a sonic welding area base plate (14) such as that illustrated in FIG. 1. The sonic welding area base plate (14) can be made of any material suitable to its purpose and may be capable of attaching a multitude of rigid mold apparatuses. The sonic welding area base plate (14) should be able to hold the rigid mold apparatus (15) in proper position for the sonic horn (13) to enter the channel (18) in the rigid mold apparatus (15). The rigid mold apparatus (15) may be attached to the sonic welding area base plate (14) by a bracketing means (20), or any other means capable of securely and releasably attaching the rigid mold apparatus (15) to the sonic welding area base plate (14). It is often preferable that the platform (14) is of a suitable construction such that it can be adjusted to have absolute parallelism with the bottom surface (13) of the sonic horn (12).

Such sonic welding area base plate (14) may also have a means to support a sonic welding apparatus (10) as illustrated in FIG. 1 such that the sonic horn (12) may be moved vertically, such means may include any apparatus or assembly that will facilitate the sonic horn's (12) entry into the channel (18) of the rigid mold apparatus (15). The rest of the sonic tool apparatus (10) should facilitate this vertical movement with the necessary support structures and assemblies.

In an embodiment of the present invention, the forth step (24) in the process of manufacturing the product is application of sonic welding with a sonic tool apparatus (10). A sonic tool apparatus suitable for performing sonic welding is illustrated in FIG. 1.

The main parts of a sonic tool apparatus may be purchased on the market and are merchandised, for example, by Branson Ultrasonic Corporation, having a place of business at Danbury, Conn. The Branson 2000IW is a suitable device for this process, but it would need to be fitted with a rigid mold apparatus (15).

While the above device is suitable, it should be noted that any ultrasonic welding tool of similar design or purpose can be used. Power ranges from 500 Watts to several kilowatts can be used, external means of applying pressure can range from 0-100 PSI, and frequency can range from 4 Kilohertz(−) to 70 Kilohertz (+); with each adjustment of power, pressure, or frequency you will alter the temperature response, maximum density, and the end texture of the material. As these characteristics are subjective to the user, a variety of different parameters could be used to produce a variety of products with differing qualities.

The sonic tool apparatus (10) has a sonic horn (12) which can be inserted into the channel of a rigid mold apparatus (18), such sonic horn has a bottom surface (13) which is adapted, in conjunction with the internal surface at the bottom of a rigid mold apparatus (15), to accomplish the sonic welding of the cannabinoid containing material (19) placed inside the rigid mold apparatus channel (18) by lowing the sonic horn (12) into the rigid mold apparatus channel (18) until it compresses the cannabinoid containing material (19) via pneumatic, hydraulic, or other means for producing pressure while sonic vibrations are produced by the sonic tool apparatus (10) and transferred to the cannabinoid containing material (19); thereby simultaneously heating and compressing the cannabinoid containing material (19). This process is illustrated in FIG. 5.

The under surface (13) of the sonic horn (12) can be tailored by the supplier at the request of the user to be substantially parallel to the sonic welding platform (14). It should be noted that the sonic horn (12) may or may not have any indentations along its side which are common to the design of sonic horns and could be construed to be definitive as to the definition of what a sonic horn is, for the purposes of this application a sonic horn is any part of a sonic tool apparatus that inserts into a rigid mold apparatus.

For optimization of the sonic welding of cannabinoid containing materials (19) the sonic horn (12) must be of adequate size to insert into the channel of the rigid mold apparatus (18) without touching the inside of the rigid mold apparatus (15) or inadequately filling the space between the rigid mold apparatus (15) and the sonic horn (12). The gap between the sonic horn (12) and the rigid mold apparatus (15) must be the minimum allowable for the sonic tool apparatus (10) as indicated by its specifications. Too wide a gap will result in extrusion of cannabinoid containing material (19) via the gap; too narrow a gap will result in contact between the rigid mold apparatus (15) and the sonic horn (12), causing: sonic energy losses, decreased efficiency, tool damage, and/or a poor quality product.

An important added benefit of sonic welding in this particular application is that pressure from compression and friction from the sonic vibrations created by the sonic tool apparatus (10) cause heat gain in the cannabinoid containing material (19), when the temperature of the cannabinoid containing material (19) then exceeds 110 degrees Celsius decarboxylation occurs, thereby activating the psychoactive properties of cannabinoids such as tetrahydrocannabinolic acid (THCA) by converting it to tetrahydrocannabinol (THC). Once the cannabinoid containing material (19) has been decarboxylated and psychoactively activated the product is ready for oral consumption. The decarboxylation of the cannabinoid containing material (19) is entirely dependent upon the temperatures achieved during sonic compression of the material. It is possible to use this same method to produce non-orally active solids by keeping temperatures below 110 degrees Celsius during processing.

Another benefit of sonic welding is that compression and elevated temperatures conferred to the cannabinoid containing material (19) cause the structure of the cannabinoid containing material (19) to melt and fuse along grain, cell, and molecular boundaries. When the cannabinoid containing material (19) solidifies thereafter it hardens into a uniform compact solid (28) of the dimensions determined by the rigid mold apparatus, sonic horn, heat gain, vibrational frequency, pressure, and duration of sonic welding. This uniform compact solid (28) is illustrated in FIG. 6.

In a preferred embodiment of the invention, an extract of the trichome of Cannabis is produced by sifting the trichome through a fine screen or other method capable of producing a material with a high concentration of cannabinoids. When this high cannabinoid containing extract material is used as the cannabinoid containing material (19) the crystalline structure (when sifted from trichome) of the extract material heats up and the individual granules and trichome structures are sonically melted and thereafter solidified, forming a uniform high density solid from the fused extract material that is psychoactive and ready for oral consumption.

To parameterize the process, perform the sonic welding operation with the cannabinoid containing material (19) while monitoring internal temperatures of the material. The processing must exceed ~110 degrees Celsius, but not exceed ~190 degrees Celsius to maintain potency and quality of product. The duration, pressure, and energy used can be tailored to fit production time constraints while maintaining the safe operating area temperatures. Excessively high processing temperature can vaporize the material, degrade it, or cause a violent eruption of gasses upon combusting the pellet during processing. Careful regulation of temperature can be used to avoid these effects. A uniform compact solid (28) of the cannabinoid containing material (19) is the end product when the materials are confined under pressure; but the active compounds, density, and texture are variable to request by altering the processing parameters.

A biomass pelleting research study (Yongjun Tang, Chunmu Chen, Guan Wang. Temperature On-Line Measured in Ultrasonic Vibration-Assisted Pelleting Cellulosic Biomass. Applied Mechanics and Materials, 2012, Vol. 151: pp. 245-249) was used to develop the safe operating areas for this method. Careful consideration and adjustment is needed to optimize these temperature responses, but this study should stand as a guide in that process. Such reference is hereby incorporated in its entirety.

In an embodiment of the present invention, the fifth step (25) in the process of manufacturing the product is removal of the uniform compact solid (28) from the rigid mold apparatus (15). After the cannabinoid containing material (19) has been compressed and heated to the desired temperature via sonic welding, energy to the sonic tool apparatus (10) can be ceased. After the energy to the device is removed, the sonic horn (12) can be retracted from the rigid mold apparatus (15). Once the sonic horn (12) is removed the rigid mold apparatus (15) can be detached, if need be, from the sonic welding base plate (14) and the uniform compact solid (28) made from the cannabinoid containing material (19) can be removed from the rigid mold apparatus (15). This is illustrated in FIG. 6.

In an automated process, the rigid mold apparatus (15) could then be moved down production line for uniform compact solid (28) removal and replaced with a newly prepared rigid mold apparatus (15) loaded with cannabinoid containing material (19) waiting to be processed. Care should be taken to ensure clean removal of the finished product, as it may become stuck to the rigid mold apparatus. To facilitate easy removal the mold can be chilled or frozen after production, but before material removal. This process can be adapted for more commercial distribution by adopting similar automation equipment to that used in performing ultrasonic plastic welding in automobile manufacture.

In an embodiment of the present invention, the sixth step (26) in the process of manufacturing the product is quality control and accurate labeling. The uniform compact solid (28) removed from the rigid mold apparatus (15) should be chemically verified with lab testing to accurately label the product with the concentrations of selected cannabinoid compounds contained therein; this information should be provided to the consumer with the suggested modes of use. If in house testing of these concentrations is performed, the results should be audited with third-party verification.

In an embodiment of the present invention, the seventh step (27) in the process of manufacturing the product is adding the decarboxylated cannabinoid containing material to other products. Once the cannabinoid containing material (19) has been decarboxylated, transformed into uniform compact solid (28), and possibly tested for potency it can be used as a base material that can be smoked, orally consumed, or added to other ingredients that are smoked or orally consumed.

Additional benefits of the described product, process, and product by process include the fact that the entire process does not require the use of any liquid or solvent of any kind to decarboxylate cannabinoids and not does require the use of heat that is not provided from the sonic vibration and pressure of sonic welding itself The temperatures attained by sonic welding assist in sterilization of the end product. Sonic welding of Cannabis increases the oil extraction from the materials by destroying its cell walls making the beneficial oils more available for metabolism. Compressing the cannabinoid containing material (19) into uniform compact solid (28) decreases the costs of transporting the material. Compressing the cannabinoid containing material (19) uniform compact solid (28) also decreases the costs of storing the material. Sonic welding decarboxylates cannabinoids in seconds to minutes, which is much faster than other commonly used methods.

Conclusion

It is to be understood that while certain forms of the invention are illustrated, it is not to be limited to the specific forms or arrangements herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantage mentioned, as well as those inherent therein. The embodiments, methods, procedures, and techniques described herein are presently representative of the preferred embodiments; are intended to be exemplary; and are not intended as limitations on the scope. Changes therein and other uses will occur to those skilled in the art which are encompassed within the spirit of the invention and are defined by the scope of the claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the claims.

What is claimed is:

1. A solid decarboxylated cannabis prepared by a process comprising:
    loading cannabis into a rigid mold apparatus;
    applying sonic welding with a sonic tool apparatus to said cannabis in said rigid mold apparatus, wherein said sonic welding causes compression, heating to at least 110° C., and decarboxylation of said cannabis; and
    removing said compressed, heated, and decarboxylated cannabis from said rigid mold apparatus, to yield said solid decarboxylated cannabis.

2. The solid decarboxylated cannabis of claim 1, wherein said application of said sonic welding is for a predetermined duration based upon the heating of the cannabis.

3. The solid decarboxylated cannabis of claim 1, wherein said compressed, heated, and decarboxylated cannabis forms a uniform compact solid.

4. The solid decarboxylated cannabis of claim 1, further comprising attaching said rigid mold apparatus to a sonic welding area base plate prior to sonic welding.

5. The solid decarboxylated cannabis of claim 4, further comprising detaching said rigid mold apparatus from said sonic welding area base plate prior to removing said compressed and decarboxylated cannabis from said rigid mold apparatus.

6. The solid decarboxylated cannabis of claim 1, further comprising combining said decarboxylated cannabis with another material.

7. The solid decarboxylated cannabis of claim 1, wherein applying sonic welding with said sonic tool apparatus comprises the use of frequencies greater than 15,000 vibrations per second.

8. The solid decarboxylated cannabis of claim 1, wherein applying sonic welding is conducted in an automated process wherein said sonic welding is applied to a series of rigid mold apparatuses.

9. The solid decarboxylated cannabis of claim 1, wherein said cannabis is a trichomic cannabis.

10. The solid decarboxylated cannabis of claim 1, wherein said cannabis has been dried.

* * * * *